United States Patent [19]

Yamada

[11] Patent Number: 4,834,119
[45] Date of Patent: May 30, 1989

[54] ARTIFICIAL HAIR FOR HAIR IMPLANTATION AND METHOD OF PREPARATION

[76] Inventor: Shiro Yamada, No. 2-7-1-606, Mita, Minato-ku, Tokyo, Japan

[21] Appl. No.: 116,326

[22] Filed: Nov. 3, 1987

Related U.S. Application Data

[62] Division of Ser. No. 13,917, Feb. 12, 1987, Pat. No. 4,793,368.

[30] Foreign Application Priority Data

May 22, 1986 [JP] Japan .............................. 61-116283
May 22, 1986 [JP] Japan .............................. 61-76349

[51] Int. Cl.⁴ .................................................. A41G 3/00
[52] U.S. Cl. .................................... 132/201; 623/15
[58] Field of Search .................. 132/5, 53, 56, 201; 623/15

[56] References Cited

U.S. PATENT DOCUMENTS 3,642,010  2/1972  Kuris ................................. 132/5
3,645,276  2/1972  Chaihyung Cho ................ 132/5
4,588,408  5/1986  Yamada .......................... 623/15

FOREIGN PATENT DOCUMENTS 2045089  10/1980  United Kingdom ........... 623/15

*Primary Examiner*—Gene Mancene
*Assistant Examiner*—Adriene J. Lepiane
*Attorney, Agent, or Firm*—Browdy & Neimark

[57] ABSTRACT

An artifical hair for implantation comprising a loop and a hair root portion is prepared by forming a loop by winding a synthetic resin monofilament around a bar shaped jig, forming an S-twisted part by twining a first end of the monofilament around the second end of the monofilament and twisting the configuration once to form an S shape at the foot at the loop, and fusion bonding the S-twisted part of the monofilament only at a region between two points where both filaments intersect each other.

6 Claims, 3 Drawing Sheets

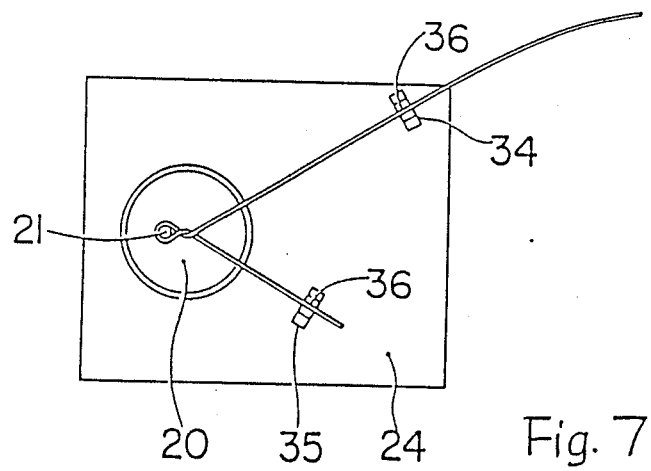
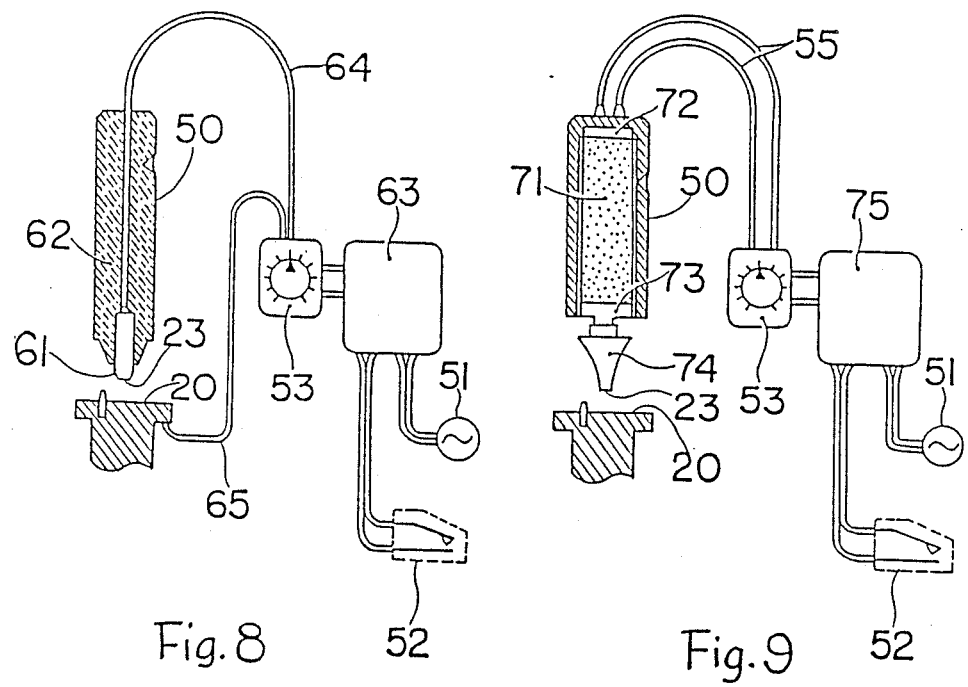

ARTIFICIAL HAIR FOR HAIR IMPLANTATION AND METHOD OF PREPARATION

This is a division of application Ser. No. 013,917, filed Feb. 12, 1987, now U.S. Pat. No. 4,793,368 issued Dec. 27, 1988.

FIELD OF THE INVENTION

The present invention relates to artificial hair to be directly implanted into the skin, and to a method of preparation thereof.

BACKGROUND OF THE INVENTION

For perhaps hundreds of years wigs have been commonly used to hide a bald head. Various types of wigs have been proposed, a recent one of which is to be found in U.S. Pat. No. 3,645,276 of Chaihyung Cho. However, a consistent problem with wigs is that they have a tendency to easily slide off the head, particularly under windy conditions or when one engages in athletics.

More recently, methods been proposed for simulating the appearance of having live hairs on the bald head. Thus, one proposal is shown in U.S. Pat. No. 3,642,010 to Kuris, where a supplemental hair consisting of natural hair or synthetic hair is joined to a live hair on the human head by the use of ultrasonic energy. However, it is very difficult to hold supplemental hairs on the human head over a long term. The supplemental hairs easily fall off after only a short term, because the live hairs are usually very thin and weak and have a tendency to break.

In recent years, artificial hair for direct implantation into human skin has been developed. However, the presently available artificial hair for implantation is not completely satisfactory because the shape of the hair root in the artificial hair does not enable the hair to be fixed firmly in place.

One proposal for solving this problem is shown in British patent 2006048A, wherein an artificial hair made of a monofilament resin has a loop part at the end thereof, the hair root being formed by tying the loop part vertically. The disadvantage of this arrangement is that the loop part is easily untied if it is wound singly. If the loop part is wound doubly or more, the knot is enlarged greatly with respect to the diameter of the hair root. When this type of hair is implanted, great injury is caused to the skin, resulting in much of the implanted hair falling out just after implantation. It is generally necessary to pull off the planted hair if inflammation or suppuration occurs on the skin after the hair has been fixed in place. However, with the artificial hair having a loop at the end thereof, if subcutaneous tissue has interpenetrated the loop part, the pulled hair is snapped off at the joint of the knot, leaving the hair root part in the skin tissue which may cause additional medical problems.

To eliminate the above disadvantages, the present inventor previously proposed, in U.S. Pat. No. 4,588,408, of yamada to provide artificial hair which can be pulled out without leaing the root part in the skin tissue. In this instance, intersecting parts of looped hair root were fusion bonded using high frequency spot welding. This gave a freely adjustable peeling strength to the intersecting parts of the hair root. Accordingly, if a planted artificial hair is pulled with a force greater than that of a specified value, the bonding is peeled at the intersection, and the loop shaped hair root becomes a single line of monofilament which can be pulled off without being left n the skin.

However, since the artificial hair is bonded at only one point of intersection at the joint of the loop shaped hair root part, considerably firm fusion bonding is necessary to obtain the critical peeling strength at the intersection, in order to bear the pulling force. If this is the case, the fusion-bonded part becomes too thin, making it more likely that the monofilament will be snapped at the thinned part. Therefore, the conditions for fusion bonding, such as the welding force of a high frequency spot welding device, welding time, frequency of welds, etc., should be controlled carefully. Therefore, the percentage of defective products may increase considerably.

SUMMARY OF THE INVENTION

It is a further object of the present invention to overcome the disadvantages of the prior art as described above.

It is a further object of the present invention to provide inexpensive artificial hair for implantation.

It is a still further object of the present invention to provide artificial hair for implantation having the appropriate critical peeling strength of the intersecting part at the joint of the loop shaped hair root, permitting pulling off of the hair root in the stage of forcible epilation without causing snapping at the hair root yet forming a single filament.

It is yet another object of the present invention to provide a process for preparing artificial hair for implantation inexpensively and in good yield while eliminating the defects of conventional artificial hair,, permittinf a high success rate of implantation, and providing such artificial hair having an apprpriate critical peeling strength at the intersecting point of a joint of a loop shaped hair root part so as to permit pulling off of the hair root part in the form of a single line when it is pulled forcibly.

These and other objects of the present invention are achieved by providing an artificial hair for hair implantation consisting of a loop part formed by winding a monofilament comprising a thermoplastic synthetic resin to form a loop, and a hair root part forming a hooked part protruding from the foot of the loop part at a certain angle to the hair root part. The monofilament of the hair root part and that of the hooked part twine around each other at the foot of the loop part in the shape of an S, and both monofilaments are bonded by fusion at the two points where the filaments intersect.

The artificial hair according to the present invention is formed by the following steps:

1. Forming a loop by winding a monofilament of a thermoplastic synthetic resin around a bar shaped jig;
2. Forming a bonded part by twining an end of the monofilament for forming the hooked part around another part of the omonfilament for forming a hair shaft part;
3. Twisting once to form an S shape twining at the foot of the loop;
4. Holding the monofilament for forming the hooked part and the monofilament for-forming the hair shaft part with a supporting tool so that said filaments are extended at a certain angle to each other;
5. Heating the bonded part under pressure in a heating zone forming a plane in a fusion bonding heater to fuse bond and fix the monofilament part only at a region between two points where both filaments intersect each other.

The monofilament of the present invention may be any thermoplastic monofilament, such as polyester, polyethylene, polyproplend, so long as the thermoplastic is not toxic to the human body. However, a polyester resin monofilament having a diameter of from about 0.06mm to about 0.1mm prepared by melt spinning a linear polymer of polyethylene terephthalate is most preferred because of its low toxicity, high heat resistance, and feel of natural hair. The fusion bonding of the monofolament of the hooked part to the monofilament of the hair shaft part at only two intersecting parts is effected by heating the parts in the heating zine of a heating device for fusion bonding. The welding pressure for this process should be from about 20 grams to about 40 grams, the heating temperature should be from about 180° C. to about 260° C., and the heating time should be from about 0.1 second to about 3.0 seconds.

Any heating device for fusion bonding, such as an electric resistance heating device, high frequency heating device, or ultrasonic heating device, which is capable of controlling the heating time, temperature,, etc., and welding pressure during heating may be useful. However, the room temperature or the ambient temperature of a working bed should be held at a constant temperature for execution of operation when an electric resistance heating device is used, because of its tendency to be easily influenced by the ambient temperature.

When a high frequency heating device is used, sufficient heating may be obtained with a device having a capacity balow 2 kW, and from about 1 MHz to about 100 MHz frequency for from about 0.1 second to about 1.0 second of heating When an automatic heating device is used, the heating result may be attained with a device having less than 1 kW capacity and from about less that 1/5 to about 10 kHz frequency for from about 0.1 to about 0.5 second heating. Since an ultrasonic heating device can be finely adjusted with repect to both temperature and region of heat application, an ultrasonic heating device is the preferred heating device for the present invention.

BRIEF DESCRIPTION OF THE DRAWINGS

FIG. 1 is a front view;

FIG. 2 is a sectional view at the line A—A in FIG. 1;

FIG. 3 is a section view at the line B—B in FIG. 1; and

FIG. 4 is a sectional view at the line C-C in FIG. 1.

FIGS. 5-9 illustrate examples of devices suited to the preparation of the artificial hair in accordance with the present invention.

FIG. 5 is an enlarged view of a part of the device obliquely from above.

FIG. 6 is a side view of the entire body of the device.

FIG. 7 is an enlarged plan of a par of the device as illustrated by FIG. 5.

FIG. 8 is a sectional view illustrating a part of the high frequency heating device used for preparing the artificial hair according to the present invention.

FIG. 9 is a sectional view of a part of an ultrasonic heating device for preparing the artificial hair according to the present invention.

DETAILED DESCRIPTION OF THR DRAWINGS

Figure 1:
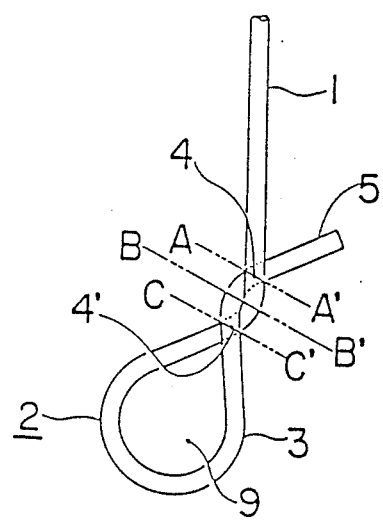
FIGS. 1-4 illustrate examples of artificial hair according to the present invention.
Figure 2:
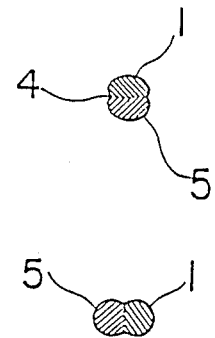
Figure 3:
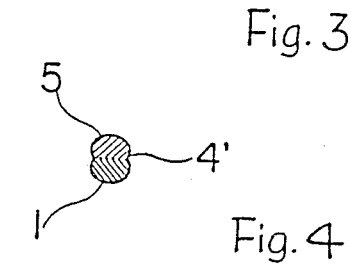
Figure 4:
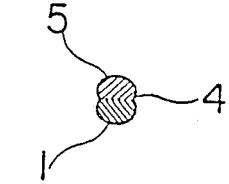

The artificial hair for implantation according to the present invention comprises, as illustrated by FIGS. 1-4, a loop part 3 formed by winding an end of a monofilament of a thermoplastic synthetic resin and a hair root part 2, consisting of a hooked part 5 protruding from the foot of the looped part 3 at a certain angle to the hair shaft part of the artificial hair 1. The monofilament forming the hair shaft part of the artificial hair 1 and the monofilament forming the hooked part 5 twine around each other at the foot of the looped part 3, forming an S shape and a part bonded by fusion bonding a region between two intersecting points 4,4'.

The thermoplastic monofilament of the present invention can be made from any thermoplastic monofilament having low toxicity to the human body, such as polyethylene, polypropylene, etc. However, the preferred monofilament is of polyester having a diameter ranging from about 0.06mm to about 0.1mm, the monofilament is obtained by melt-spinning a linear polyethylene terephthalate. This monofilament is most preferred because of its extremely low toxicity, high heat resistance, and texture and feel of natural hair.

To form a hair root part 2 having the shape as shown in FIG. 1, a bonded part 6 is formed by holding both ends of the monofilament cut to an appropriate length, winding the monofilament around a bar jig, fixing the intersected points of the artificial hair by twisting the hair by one turn, and heating the intersected part momentarily under pressure in a heating zone of a heating device. The heating device may be an electric resistance heating device, a high frequency heating device, an ultrasonic heating device, etc. The intersected part is heated to effect fusion bonding of the two intersected points 4,4'.

The peeling strength of the bonded part 6 of the artificial hair should be controlled in accordance with the present invention to such a degree as to permit peeling of the fusion-bonded intersected parts to cause pulling off of the hair by the forcible pulling after implantation without causing snapping of the hair root. The critical strength should range from about 100 grams, and, preferably, from 140 grams to 200 grams against a load in the direction of the hair shaft.

For this purpose, the bonded part should be heated at from 180° C. to 260° C. for from about 0.1 second to 3.1 seconds momentarily under from about 20 to 40 grams load in a heating device for fusion bonding.

The hair root part 2 formed by the process of the present invention consists mainly of a loop part 3 and a hooked part 5, but both are so small that the outside diameter of the loop part 3 is at largest from 0.8mm to 1.5mm, and at least from 0.01mm to 1.3mm. The length of the hooked part 5 ranges from about 0.3mm to about 1.5mm.

The hole 9 formed in the inside of the loop part serves to insert a bifurcated part at the tip end of thr hair implanting needle during hair implantation, functioning also to prevent epilation of planted hair.

In the following, an example of the process for preparing the artificial hair in accordance with the present invention is explained by referring to FIGS. 5-9.

Figure 5:
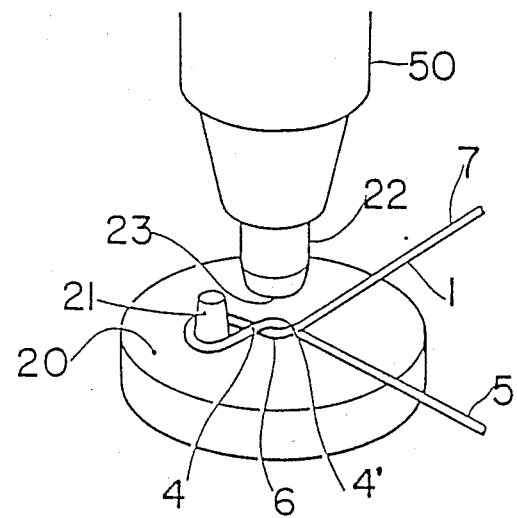

A line of monofilament 1 cut to an appropriate length was wound around a bar shaped jig 21 by holding both ends of the monofilament as shown in FIG. 5, and the monofilament was fixed by twisting one turn at the intersecting part of the artificial hair at both ends. The intersecting parts were heated momentarily under pressure in a flat heating zone 23 of a heating bar 22 of a fusion bonding heating device 50, for example, an electric resistance heater, a high frequency heater, or an ultrasonic heater, to form a bonded part 6 by fusion bonding a region between two intersection points 4,4'.

According to the present invention, the peeling strength of the artificial hair at the bonded part 6 should be controlled to a degree permitting peeling at the fusion-bonded intersecting points so as to allow the monofilament to be pulled off in the form of a single string in the stage of forcible epilation after implantation without causing snapping of the hair root part. This peeling strength should be from about 100 to about 200 grams, preferably from 140 grams to 200 grams against a load in the longitudinal direction of the hair root part.

For this purpose, the bonded part should be heated momentarily in a heating zone 23 of a heating device 50 for fusion bonding at from about 180° C. to about 260° C. for from about 0.1 second to about 3.0 seconds under from about 20 to about 40 grams of pressure.

Figure 6:
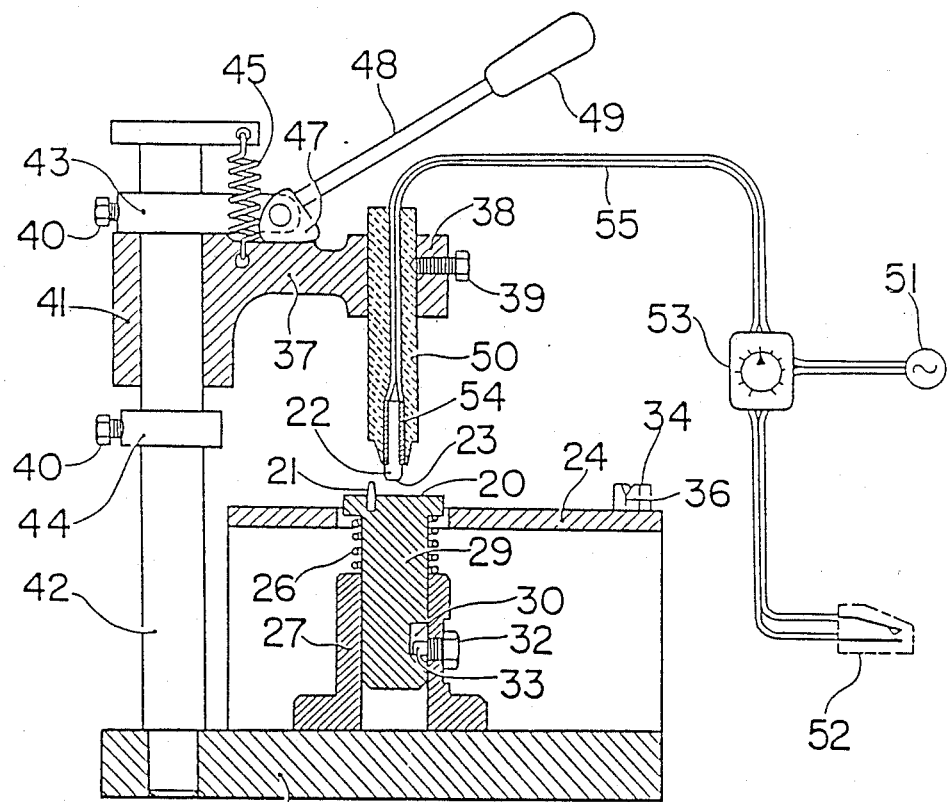

A device suitable for preparing the artificial hair according to the present invention is illustrated in FIGS. 6 and 7. A cylindrical sliding body 29 is provided to a rear surface of a work table 20 disposed with a bar shaped projection 21, which is fitted freely slidably to a cylinder 27 provided on a base 28. A spring 26 which actuates the work table 20 and the clyinder 27 in the opposite direction to each other is attached between the rear surface of the work table 20 and the cylinder 27. An adjusting groove 30 is engraved on the side wall of the sliding body 29, and the distance of the sliding body by the vertical movement is controlled by the protrusion of a pin 33 at the top end of a screw 32 which is screw-fitted to the side wall of the cylinder 27, toward the inside of the adjusting groove.

On one hand, a sliding ring 41 of a supporting arm 37 is fitted vertically slidably to a stanchion 42 provided protruding from the base 28. Further, adjusting rings 43, 44 for controlling the vertical movement of the supporting arm 37 are fixed to the stanchion 42 by a screw 40. Also, the supporting arm 37 is pulled by a spring 45 fixed at one end to a stanchion 42 so as to be lifted always upward. A supporting ring 38 is provided at another end of the supporting arm 37, the supporting ring holding a heating device 50 by a screw 39.

A revolving cam 47 turned by a handle 48 contacts the supporting arm 37. Thus, the supporting arm 37 is moved vertically by the revolution of the cam 47.

An electric resistance heater 54 is built into the heating device 50. The bonded part of an artificial hair is pressed and heated simultaneously in a flat heating zone 23 formed on the foot surface of a heating bar 22 which connects thermally to a heater 54. The heater 54 is connected to a power source 51 by a cord 55, but a foot switch 52 and a timer device 53 are provided in the circuit.

When the heating device is a high frequency heater, as illustrated in FIG. 8, the heating device comprises an insulating body 62 and a hot pressing rod 61 comprising a dielectric body such as an iron housed in the insulating body. A flat heating zone 23 is provided to the foot surface of the hot pressing rod 61, and another cord 65 is connected to a part of the work table 20. Further, a foot switch 52 and a timer device 53 are also provided in the circuit.

When the heating device is an ultrasonic heater, as illustrated in FIG. 9, an ultrasonic oscillator 71 consisting of a ceramic piezoelectric body is built into the heating device. Electrodes 72, 73 provided to the top and foot surface of the electronic oscillator 71 are connected by a cord 55 to an ultrasonic wave generator 75, and a foot switch 52 and a timer device 53 are also provided in the circuit. Further, a heating horn 74 is fixed to the foot end of the ultrasonic oscillator 71, and a flat heating zone 23 is formed on the foot end of the heating horn 74.

In accordance with the present invention, the artificial hair is prepared by gripping a grip 49 disposed in the device shown in FIG. 6, and turning the revolving cam 47 by turning a handle 48 upward to move the supporting arm 37 upward. Then, the artificial hair 1 having a hair shaft part 7 (see FIG. 5) is wound around the bar shaped projection 21 on the work table 20 and twisted one turn, fixing both ends of the artificial hair 1 by inserting them into slits 36 in each retaining piece 34, 35 on the stationary table 24. When the handle 48 is turned downward and the supporting arm 37 is moved downwardly by the cam, the S-shaped intersecting part of the artificial hair is pressed by the heating area 23 of the heating device 50, and the work table 20 is pushed downward against the force of the spring 26. In this stage, the pressing load on the intersecting parts 4,4' of the artificial hair 1 is adjusted to the desired value, i.e., from 20 grams to 40 grams, by adjusting the force of the spring 26 and the distance of the movement of the supporting arm, that is, the moving distance of the work table.

When the foot switch 52 is closed, the heater 54 is actuated, and the intersecting parts 4,4' of the artificial hair 1 are heated by the heating zone 23 at the end of the heating bar 22. Fusion bonding of the area between the intersecting points 4,4' alone is achieved by setting the heating time at from 0.5 second to 3.0 seconds previously with a timer device.

When a high frequency heater is used, as shown in FIG. 8, the frequency of the high frequency generator 63 is set from 1 MHz to 100 MHz, and the timer device 53 is set from 0.1 second to 1.0 second. Since the artificial hair is a dielectric material, the intersecting part of the artificial hair alone is brought into press contact with the flat heating zone 23 of the hot pressing rod 61 by the effect of the high frequency electric field, and the part is fusion bonded.

As shown in FIG. 9, When an ultrasonic wave heater is used, the frequency of the ultrasonic wave generator 75 is set from about 1.5 kHz to about 10 kHz, and the timer is set from about 0.1 second to 0.5 second. Thus, vertical oscillation having the frequency of ultrasonic wave region generated by the piezoelectric element 71 is transmitted to the part of the artificial hair to be bonded through the heating zone 23 of the heating horn 74, and the intersecting part of the artificial hair is heated by the heat generated by the internal friction. Thus, bonded part 6 is obtained.

The artificial hair 1 formed by the method of the present invention is provided with a loop 3 at the tip end of the hair shaft part 7 and a hooked part 5 protruding with a certain angle to the hair shaft part 7, as illustrated by FIG. 1. A bonded part 6 is formed by fusion bonding the monofilament for forming the hooked part 5 only at a part between two intersecting parts 4,4'. Also, the hole 9 formed at the inside of the looped part 3 is for inserting the bifurcated part 14 of the tip end of the hair-implanting needle 13 in the process of hair implantation, which also serves to prevent the hair from falling off after implantation.

Figure 10:
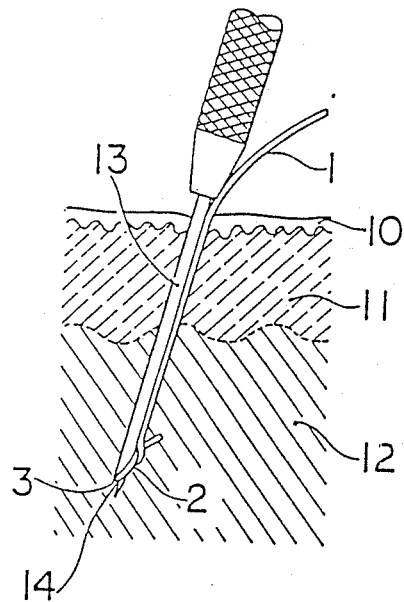
FIG. 10 is an illustration of the process for implanting the artificial hair according to the present invention.
Figure 11:
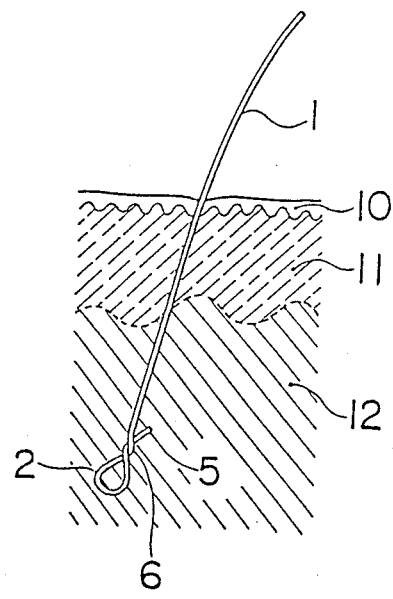
FIG. 11 shows the condition of the artificial hair implanted in the skin.

As illustrated in more detail in FIG. 10, if the rear side of the loop 3 is held by the bifurcated part 14 of the hair implanting needle 13, the hair root part 2 is thrust into the deep part of the subcutaneous tissue 12, breaking through epidermis 10 and corium 11. The implanting needle is then pulled out gently by itself, the hair root part 2 is fixed in the subcutaneous tissue 12, and the artificial hair is prevented from coming back since the hooked part 5 of the hair root part 2 protrudes at a certain angle to the hair shaft part 7 as illustrated in FIG. 11.

The hair root part 2 is held securely when the subcutaneous tissue in the hole 9 of the hair root part 2 is restored after several days, and fibrillation of the tissue around the artificial hair progresses. Thus, falling off of the planted artificial hair is completely prevented.

Since the size of the bonded part of artificial hair 1 is very fine as compared to artificial hair made by other processes, the injury to the subcutaneous tissue during hair implantation is much less, and falling off of the artificial hair immediately after implantation is greatly reduced. Moreover, the tissue injured by the implantation is restored more quickly, so that a characteristic high success rate is obtained in the hair implantation according to the present invention.

Further,ore, even if suppuration or inflammation occurs after hair implantation, the implanted hair is pulled rapidly by pulling with a force greater than 100 grams without leaving snapped hair root in the subcutaneous tissue, i.e., without danger of adversely affecting the tissue, because the fusion-bonded part between the intersecting points 4,4'is peeled by the pulling, transforming the hair root part to a single line of monofilament.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A process for preparing artificial hair for hair implantation from a synthetic resin thermoplastic monofilament having a first part terminating in a first end and a second part terminating in a second end comprising:
    forming a loop by winding the monofilament once around a bar shaped jig;
    forming a bonded part by twining the first part of the monofilament around the second part of the monofilament;
    twisting the monofilament once to form an S shape at the foot of the loop while holding the first and second parts with a supporting tool so that the first and second parts are extended at a predetermined angle to each other to form contacted parts;
    heating said contacted parts, under pressure in a heating zone forming a plane, in a fusion bonding heater to fuse-bond the monofilament at a region between two points where both filaments intersect each other.

2. The process of claim 1 wherein the monofilament of synthetic thermoplastic synthetic resin is formed by drwaing a resin selected from the group consisting of polyester resin, polyethylene resin, and polypropylene resin, to a monofilament having a diameter ranging from about 0.06mm to about 0.1mm.

3. The process of claim 1 wherein the heater for fusion bonding is an electric resistance heating device.

4. The process of claim 1 wherein the heater for fusion bonding is a high frequency heating device.

5. The process of claim 1 wherein the heater for fusion bonding is an ultrasonic heating device.

6. The process of claim 1 wherein said contacted parts pressed and heated at from about 180° C. to about 260° C. under pressure ranging from about 20 grams to about 40 grams for a time ranging from about 0.1 second to about 3.0 seconds.

* * * * *